United States Patent [19]

Tavlarides et al.

[11] Patent Number: 4,726,221

[45] Date of Patent: Feb. 23, 1988

[54] ULTRASONIC MEASUREMENT OF DISPERSED PHASE VOLUMETRIC HOLDUP IN LIQUID/LIQUID DISPERSIONS

[75] Inventors: Lawrence L. Tavlarides, Fayetteville, N.Y.; Julio C. Bonnet, Caracas, Venezuela

[73] Assignee: Syracuse University, Syracuse, N.Y.

[21] Appl. No.: 914,370

[22] Filed: Oct. 2, 1986

[51] Int. Cl.$^4$ .............................................. G01N 29/02
[52] U.S. Cl. ................................... 73/61.1 R; 73/597
[58] Field of Search ............................. 73/61.1 R, 597

[56] References Cited

U.S. PATENT DOCUMENTS

| | | | |
|---|---|---|---|
| 3,892,127 | 7/1975 | Cirulis et al. | 73/61.1 R |
| 4,080,837 | 3/1978 | Alexander et al. | 73/597 X |
| 4,236,406 | 12/1980 | Reed et al. | 73/597 X |
| 4,522,068 | 6/1985 | Smith | 73/597 X |
| 4,630,482 | 12/1986 | Traina | 73/597 |
| 4,656,869 | 4/1987 | Zacharias | 73/597 |

OTHER PUBLICATIONS

Bonnet and Jeffreys, AIChE J. 1985, 31(5), 788.
Hoffer and Resnick, Chem. Eng. Sci. 1975, 30, 473.
Burdett, et al., Chem. Eng. Sci. 1981, 36, 1981.
Jiricny and Prochazka, Chem. Eng. Sci. 1980, 35, 2237.

Primary Examiner—Michael J. Tokar
Assistant Examiner—Joseph W. Roskos
Attorney, Agent, or Firm—Bruns and Wall

[57] ABSTRACT

The fractional volumetric holdup $\phi$ of a dispersed phase in a two liquid dispersed phase system is determined by measuring the travel time of ultrasonic pulses on a fixed path for the dispersed phase, and for the two liquids separately, and caluclated according to the relation $$\phi = t^* - t_1 / t_2 - t_1$$

where $t^*$, $t_1$, and $t_2$ are the ultrasonic pulse travel times through the dispersed phase, the first liquid, and the second liquid. The pulses can be transmitted from a transmitter transducer straight through the contents of a reactor to a receive transducer, or can be reflected off a die or similar flat faced member back to the originating transducer.

14 Claims, 3 Drawing Figures

ULTRASONIC MEASUREMENT OF DISPERSED PHASE VOLUMETRIC HOLDUP IN LIQUID/LIQUID DISPERSIONS

BACKGROUND OF THE INVENTION

This invention relates generally to measuring methods and apparatus for measuring, and is more particularly directed to the measurement of the relative amounts of a first and second liquid, where one liquid is held up or suspended in a liquid/liquid dispersed phase system. The invention is directed more specifically to a system in which the travel time of ultrasonic pulses through the liquid/liquid dispersion is employed to derive the fractional volumetric dispersed phase holdup of the two-liquid dispersed phase system.

Previously, the measurement of the dispersed phase fractional volumetric holdup in two-phase liquid systems has been attempted by such techniques as displacement, pressure differentials, direct sampling, light beam attenuation, and electroresistivity. While these approaches can be employed to derive a result, none of them permits estimation or monitoring of the dispersed phase fractional volumetric holdup under steady state process conditions or during transient conditions. Consequently, none has proved entirely effective for monitoring the dispersed phase fractional volumetric holdup for liquids within a reaction vessel.

The dispersed phase fractional holdup is an important measure of the efficacy of a chemical reaction betweem two liquids, as it corresponds to the relative mass transfer area of one liquid to the other. Consequently, real-time accurate knowledge of this quantity permits optimization of liquid flow rates to carry out the chemical reaction with minimal waste and consistent product.

One previous approach to ultrasonic measurement of this quantity employed a sound velocimeter that was immersed in the liquid/liquid dispersion. This technique had the drawback of interfering with the flow of liquids through the reactor vessel.

OBJECTS AND SUMMARY OF THE INVENTION

Accordinly, it is an object of this invention to provide method and apparatus for measuring the dispersed phase fractional volumetric holdup in an ongoing process involving a liquid/liquid dispersion, and which avoids the drawbacks of the prior art.

It is another object of this invention to provide a technique for measuring the dispersed phase fractional volumetric holdup in which the measurement is non-invasive and non-intrusive.

It is still another object of this invention to provide such a technique in which the measurement devices are disposed externally of the process vessel, avoiding disturbance of flow patterns of the fluids within the process vessel and avoiding contact of the active surfaces of the measurement devices with possibly corrosive chemicals within the vessel.

The above objects are achieved by measuring the travel time of an ultrasonic pulse, over a fixed path, through the liquid/liquid dispersion, and comparing such travel time with the travel time of the ultrasonic pulse over the same path through each of the two liquids when in substantially pure form. The dispersed pulse fractional volumetric holdup, expressed as the symbol $\phi$, is then calculated according to the relationship.

$$\phi = t^* - t_1 / t_1 - t_2$$

where $t_1$ and $t_2$ are the travel times of the ultrasonic pulses through the pure form liquid phases, and $t^*$ is the travel time of the ultrasonic pulses through the dispersed phase system.

This measurement of $\phi$ is carried out with one or more ultrasonic transducers preferably disposed externally of the process vessel, but in acoustic communication with its contents. The ultrasonic pulses are produced in one of the transducers, and then either pass diametrically across the vessel to a pickup transducer or are reflected and return to the originating transducer. Thus, the transducer or transducers emit a train of ultrasonic pulses which traverse a predetermined path through the vessel contents. A circuit for electrically exciting the transducer or transducers and sensor circuitry for sensing the presence of the received pulses are connected to the transducers, and a device, e.g. an oscilloscope or a digital processor, is connected to the sensor circuitry to permit calculation of the pulse travel times $t^*$, $t_1$ and $t_2$, and then to carry out computation of the dispersed phase fractional holdup $\phi$ according to the above relation.

To calibrate the system, the vessel is first filled with one of the pure liquids, and the pulse travel time $t_1$ is measured and stored. Then the vessel is emptied and filled again with the other pure liquid, and the pulse travel time $t_2$ is measured and stored.

Thereafter the process is carried out using the two liquids with the one being dispersed as very small droplets in the other. The travel time $t^*$ of the ultrasonic pulses through the dispersion is monitored continuously through the process, and the dispersed phase holdup is continuously computed. The process feed rates, or other suitable parameters, can be controlled to keep the fractional holdup value of $\phi$ optimal. If the process temperature is expected to fluctuate, various values of $t_1$ and $t_2$ can be stored, for several respective temperatures, to account for temperature variations in the speed of acoustic waves through the liquids.

In a favorable embodiment the process reactor vessel is a column having baffles spaced along its axis to divide the column into compartments, and a mixing arrangement for dispersing the fluids includes a rotating shaft with at least one turbine impeller disposed within each such compartment. In a first version, the shaft diameter is smaller than the diameter of the radiating element of the emitting transducer, so that the presence of the shaft does not obstruct the path of the ultrasonic pulses. In a second version where the impeller shaft is of large diameter, flat-faced members, e.g. cubes or dice, are incorporated into the shaft to reflect the pulses back to the transducer. In this version, a synchronizer matches the timing of the ultrasonic pulses with the shaft rotations, so that the dice will be properly positioned to reflect the ultrasonic pulses back to the transducer.

For optimal results, it should be observed that the velocity of ultrasound pulses in liquid dispersions is linearly related to the dispersed phase fractional volumetric holdup $\phi$ where the dispersed liquid droplets are of a dimension as large as or larger than the ultrasound wavelength. That is, the ultrasound frequency is selected so that the wavelength is somewhat less than the expected dispersed phase droplet size.

It should be seen that the dispersed phase volumetric holdup can be continuously monitored, and that the monitoring does not interfere with the process operation. The liquids do not contaminate or corrode the ultrasonic transducers, as the transducers are disposed outside the vessel. It is unnecessary to measure or know the path length per se, for the ultrasonic pulses, as the value of the fractional holdup $\phi$ depends only on the differences in the overall travel time of the ultrasound pulses.

The above and many other objects, features, and advantages of this invention will be more fully understood from the ensuing detailed description of certain preferred embodiments, which is to be read in conjunction with the accompanying drawing.

DETAILED DESCRIPTION OF THE PREFERRED EMBODIMENT

Figure 1:
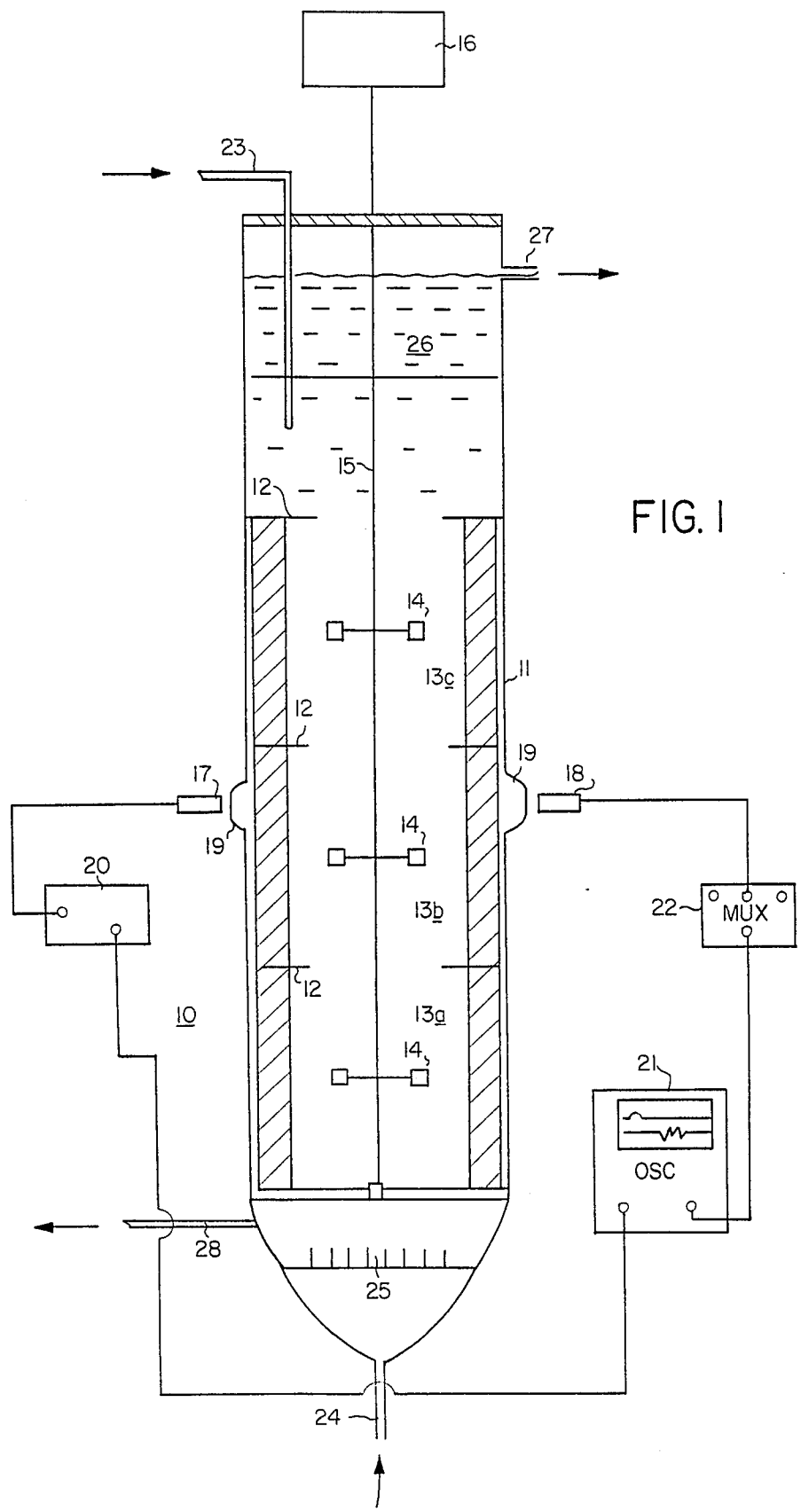
FIG. 1 is a schematic view of an extraction column arranged according to a first embodiment of this invention.

With reference to the drawing, and initially to FIG. 1 thereof, a continuous extraction reactor 10 is formed of a glass pipe column or vessel 11 ten cm in diameter and fifty cm high with baffles 12 along its axial dividing the vessel interior into fully baffled, agitated compartments 13a, 13b, 13c. Mixing of two liquid phases in counterflow within the column 11 is carried out mechanically by means of three turbine impellers 14, here of 33 mm diameter, mounted on a 9.5 mm shaft 15 at the axis of the vessel 11. The shaft 15 is rotationally driven by a 1/16 horsepower electric motor 16. The turbine impellers 14 are positioned centrally at each compartment 13a, 13b, 13c.

Two piezoelectric ultrasonic transducers 17 and 18 are located outside the vessel, each having an operative face against a respective flared flat ground-glass window 19. The windows 19 are situated diametrically opposite one another so that the transducers 17 and 18 face one another on a horizontal plane. The ultrasonic transducers 17 and 18 are in acoustic communication, through these windows 19, with the contents of the vessel 11. The transducers 17, 18 have their natural frequency in the range of 0.5 MHz to 1.0 MHz and the diameter of the operative or radiating face of the transducers is about 1.2 to 2.5 cm.

A pulse generator 20 is connected to the transducer 17, which serves as the transmitting element, and to one channel of a four-channel oscilloscope 21. The other transducer 18, which serves as the receive element, is connected through a multiplexer 22 to another channel of the oscilloscope 21. While not shown here specifically, there can be pairs of transducers 17, 18 and windows 19 at each of the compartments 13a, 13b, 13c, and the multiplexer 22 lets the oscilloscope 21 display the traces of the receive transducers 18 at each level, so the fractional holdup $\phi$ can be monitored at different column heights.

An aqueous feed 23 and an organic feed 24, supplied from respective peristaltic pumps, introduce the first and second liquids into the column 11 above the compartment 13c and below the compartment 13a, respectively. A relatively light organic dispersed phase enters the column 11 through a multi-hole glass distributor plate 25 located just below the bottom agitated compartment 13a. The coalesced organic dispersed phase collects at a top portion 26 of the column 11, and is removed via an overflow outlet 27. The processed aqueous continuous phase flows out by gravity through an outlet 28 at the bottom of the column.

Once the two liquid phases are dispersed by motion of the impellers 14, the phase generator 20 is turned on and this feeds a train of rectangular pulses of adjustable width and frequency to the transducer 17. The latter in turn emits a train of ultrasonic pulses. These ultrasonic pulses travel through the dispersion and are received at the receive transducer 18, where they are converted into electrical output signals. The transducer output signals are then amplified and displayed on the oscilloscope 21. The pulse generator 20 also sends the pulse train to the oscilloscope to trigger the oscilloscope horizontal sweep. Thus, both the signal applied to the transmitter transducer 17 and the signal produced at the receiver transducer 18 are displayed simultaneously on the oscilloscope screen. The calibrated delay sweep of the oscilloscope is used to measure the travel time $t^*$ of the pulse-through ultrasonic pulses.

To calibrate for the travel times $t_1$ and $t_2$, the column is filled first with only the aqueous phase and then only with the organic phase, and the same procedure is used to read the respective travel times $t_1$ and $t_2$ on the oscilloscope 21. Once these values are established, they can be used for the continuous calculation of the fractional holdup value $\phi$, using the relationship mentioned above.

Figure 2:
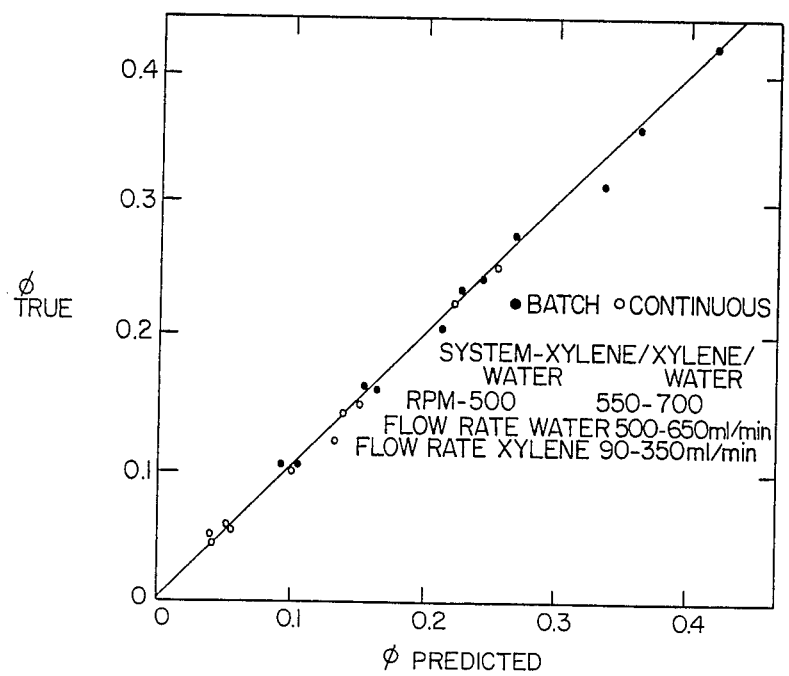
FIG. 2 is a chart showing experimental versus predicted results in the extraction column of FIG. 1 and in a batch reactor (not shown).

The results of fractional holdup measurement using this technique match very closely the results obtained using the more traditional "displacement technique." The latter involves simultaneously closing off all feeds 23, 24 and outlets 27, 28 to and from the extraction column, and then measuring the volume of the coalesced dispersed phase collected in one of the column ends. The results of this comparison are shown with the open circles in FIG. 2. The results of this technique in a batch process vessel were also compared with results of batch process agitation in a glass beaker of 10 cm diameter, 10 cm height, with a centrally located agitator shaft and a turbine impeller, and with four metal baffles of 1 cm width disposed at 90 degree intervals. The results of this comparison are also shown in FIG. 2 with the black circles.

The presence of a solute or solutes in either phase may affect the velocity of sound in the dispersion. However, this technique is still quite valid if calibration curves for both single liquid phases are obtained, to permit compensation of the values of $t_1$, $t_2$ and $t^*$ for concentration effect. Similarly, if the process is non-isothermal, temperature compensation for sound velocity is required. This can be done by measuring and storing values of $t_1$ and $t_2$ over several temperatures of interest.

The positioning of the shaft 15 at the axis of the column 11, i.e., directly in the middle of the acoustic path, does not interfere with the preparation of the ultrasound pulses, and thus does not affect the measurement of the travel time $t^*$. This lack of interference comes about at least in part because the diameter of the radiating face of the transducer 17 is larger than the diameter of the shaft 15. If the diameters were of comparable size, or the shaft diameter greater than the face diameter, then an alternative approach should be taken, such as the following.

Figure 3:
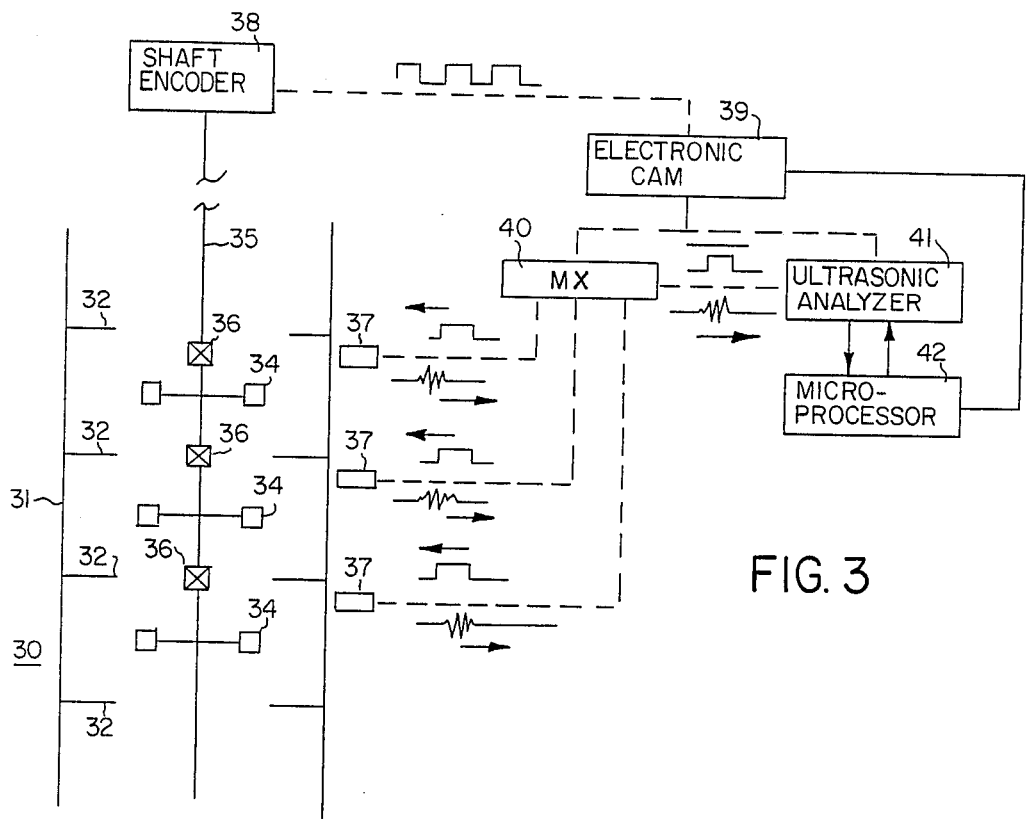
FIG. 3 is a schematic view of a reactor incorporating a second embodiment of this invention.

FIG. 3 illustrates a process reactor 30 according to a second embodiment of this invention which similarly to the first embodiment, has a glass reactor column or vessel 31 with baffles 32 that divide the interior of the column into a number of compartments 33, and with turbine impellers 34 mounted on a rotating shaft 35 disposed on the central axis of the column 31. In this embodiment, the diameter of the shaft 35 is larger than in the previous embodiment, and it significantly interferes with the ultrasonic wave front and renders the system acoustically opaque to straight-through sound transmission. In order to avoid that problem, a pulse echo technique is employed. This technique applies generally the same principles as the pulse through transmission technique, but the ultrasound pulses emitted by the transducer are totally reflected by a substantially flat surface on the shaft itself and the echoes are received either by the same transducer or by a receiver transducer disposed at or in the vicinity of the location of the transmitter transducer.

To effect this, cubes or dice 36 are mounted to rotate with the shaft 35. These dice 36 are made of a material of acoustic impedance $Z_2$ much greater than the acoustic resistance $Z_1$ of the fluid contents of the column 31, that is $Z_2 >> Z_1$, or more specifically $Z_2/Z_1 \geq 30$.

Dual element transducers 37 are disposed outside the column 31 at the levels of each of the dice 36 and facing towards the shaft 35.

To ensure that the transducers 37 are energized at the times that the dice 36 are oriented facing them, an incremental shaft encoder 38 is mounted on the shaft 35 and supplies shaft synchronization pulses to an electronic cam 39. The latter provides a channel select signal and pulse trigger signals to a multiplexer 41 which sends actuating pulses to each of the transducers 37. This system ensures synchronization of the ultrasound pulses with the shaft position, such that the arriving wavefront of the ultrasound pulses strikes the cubes or dice 36 when the flat face thereof is normal to the acoustic path, and the pulses are reflected back with a maximum energy to the receive elements of the transducers 37.

An ultrasonic analyser 41 is connected to the multiplier 40 and to the electronic cam 39 to sense the returned echo pulses, and a microprocessor control 42 is connected to the analyzer 41 and to the cam 39 to control the measurement process automatically, and also to automatically measure the ultrasound pulse travel time $t^*$ and compute the dispersed phasee fractional volumetric holdup $\phi$. The electronic cam 39 is a solid state digital electronic circuit that converts the angular position of the shaft (as based on pulses from the shaft encoder 38) into a series of channel select and channel fire signals.

The operation of the reactor 30 of FIG. 3 is similar to that of FIG. 1. The transmitter/receiver ultrasonic transducer 37 emits an electronic pulse upon stimulation by a voltage pulse signal from the multiplexer 40 and ultrasonic analyser 41. The pulse travels through the dispersion in the vessel 31 until it is reflected at the liquid-dice interface. Then, the reflected pulse travels back through the dispersion and is converted to an electrical signal by the transducer 37. This signal is channeled through the multiplexer 40 to the ultrasonic analyser where it is amplified. The time difference between the transmitted and detected pulses is calculated in the microprocessor 42, the time difference, i.e. $t^*$, being the travel time of the pulse along the round-trip path in the dispersion.

This value of travel time $t^*$ is simply fit into the above equation, together with values of travel time $t_1$ and $t_2$, similarly measured for pulses through the pure liquids, and the dispersed phase fractional volumetric holdup $\phi$ is computed.

While this invention has been described in detail with reference to particular embodiments, it should be understood that many modifications and variations would be apparent to those of skill in the art without departing from the scope and spirit of the invention, as defined in the appended claims.

What is claimed is:

1. A process of measuring a dispersed phase fractional volumetric holdup in a two-liquid dispersed phase system, comprising measuring the travel time for an ultrasonic pulse over a predetermined distance through each of the two liquid phases in substantially pure form and through the two-liquid dispersed phase system; and calculating the dispersed phase fractional volumetric holdup $\phi$ according to the relationship $$\phi = t^* - t_1/t_1 - t_2$$

where $t_1$ and $t_2$ are the travel times of the ultrasonic pulses through the pure form liquid phases, and $t^*$ is the travel time of the ultrasonic pulses through the dispersed phase system.

2. The process of claim 1 wherein said ultrasonic pulses are chosen to have a wavelength no greater than an expected average droplet size of the dispersed phase liquid.

3. The process of claim 1 wherein said travel times are measured independently of the predetermined distance travelled by the ultrasonic pulses.

4. The process of claim 1 wherein said two liquid dispersed phase system is contained within a reactor having a reactor wall, and said measuring of the travel times of ultrasonic pulses is carried out by generating a train of ultrasonic pulses in an electrically excited ultrasonic transducer disposed outside the reactor wall and in acoustic communication therewith, receiving said pulses in an ultrasonic receiving transducer disposed outside said reactor wall and in acoustic communication therewith, and electronically sensing the pulse transmission and pulse reception at said transducers.

5. The process of claim 4 wherein said reactor is a reaction column with a shaft of a predetermined diameter therein providing agitation for said two-liquid dispersed phase system, and said transducers have face diameters greater than the diameter of said shaft to avoid interference by said shaft with the travel of said ultrasonic pulses between said transducers.

6. The process of claim 1 wherein said two-liquid dispersed phase system is contained within a reactor having a reactor wall and means within the reactor for reflecting said ultrasonic pulses, and said measuring of said travel times of ultrasonic pulses is carried out by generating a train of ultrasonic pulses in an electrically excited ultrasonic transducer disposed outside the reactor wall and in acoustic communication therewith, reflecting said pulses on said reflecting means back to said transducer, receiving the reflected ultrasonic pulses in said transducers, and electronically sensing the pulse transmission and pulse reception at said transducer.

7. In a reactor of the type in which first and second liquid phases are mixed to form a two liquid dispersed phase system with one of the liquid phases being held up as a liquid/liquid dispersion in the other liquid phase, including a reactor vessel having a vessel wall within which the two-liquid system is contained, means for introducing the first and second liquids into said vessel, and mixing means for mechanically agitating the liquids; the improvement comprising ultrasonic transducer means disposed in acoustic communication with the two-liquid dispersed phase system in said vessel for transmitting a train of ultrasonic pulses into said two-liquid dispersed phase system and for receiving said pulses after they have traveled through said two-liquid dispersed phase system over a predetermined path; means for electrically exciting said transducer means to generate said ultrasonic pulses; means for sensing the pulse reception at said transducer means; and means permitting measurement of the travel time t* of said ultrasonic pulses over said predetermined path such that a dispersed fractional holdup $\phi$ of the two-liquid dispersed phase system can be calculated according to the relationship $$\phi = t^* - t_1 / t_1 - t_2$$

where $t_1$ and $t_2$ are travel times of said ultrasonic pulses through the first and second phases in substantially pure form.

8. The reactor of claim 7 in which said vessel is a column having baffles along its axis to divide the column into a plurality of compartments.

9. The reactor of claim 7 wherein said mixing means includes a rotating shaft having a predetermined diameter and having at least one turbine impeller attached thereto; and said transducer means includes a radiating element with a lateral extent exceeding the diameter of said shaft.

10. The reactor of claim 7, wherein said transducer means includes an emitting transducer element and a receive transducer element, each disposed on the outside of the vessel and diametrically opposite one another.

11. The reactor of claim 10 in which said vessel wall has flat windows formed thereon through which said transducer elements communicate acoustically with said two-liquid dispersed phase system.

12. The reactor of claim 7 in which said transducer means includes a combined transmit/receive transducer element adapted both to transmit said ultrasonic pulses and to receive the same; and said vessel includes means to reflect the ultrasonic pulses back to said transducer element.

13. The reactor of claim 12 in which said mixing means includes a rotating shaft in said vessel and at least one turbine impeller attached thereto; and said reflecting means includes a flat faced member mounted on said shaft in line with said transducer element.

14. The reactor of claim 13 in which said means for electrically exciting said transducer means includes a pulse trigger generator coupled to said transducer element and synchronizing means coupled to said shaft and to said pulse trigger generator so as to energize said transducer element to emit said pulses when said flat-faced member is oriented so as to reflect the pulses to said transducer element.

* * * * *

UNITED STATES PATENT AND TRADEMARK OFFICE
CERTIFICATE OF CORRECTION

PATENT NO. : 4,726,221

DATED : Feb. 23, 1988

INVENTOR(S) : Lawrence L. Tavlarides and Julio C. Bonnet

It is certified that error appears in the above-identified patent and that said Letters Patent is hereby corrected as shown below:

In Claims 1 and 7, please change

"$\phi = t^* - t1 / t1 - t2$"

to:

$$-- \phi = \frac{t^* - t_1}{t_1 - t_2} --$$

Signed and Sealed this

Twenty-fifth Day of October, 1988

*Attest:*

DONALD J. QUIGG

*Attesting Officer*     *Commissioner of Patents and Trademarks*